United States Patent [19]

Bhutani et al.

[11] 4,045,502

[45] Aug. 30, 1977

[54] PROCESS FOR PRODUCING HIGH PURITY PARA-CHLOROBENZOTRIFLUORIDE

[75] Inventors: Sudhir K. Bhutani, Orange; Willard A. Nichols, Madison, both of Conn.

[73] Assignee: Olin Corporation, New Haven, Conn.

[21] Appl. No.: 727,813

[22] Filed: Sept. 29, 1976

[51] Int. Cl.$^2$ .............................................. C07C 25/14
[52] U.S. Cl. .................................................. 260/651 F
[58] Field of Search ...................................... 260/651 F

[56] References Cited

U.S. PATENT DOCUMENTS 3,859,372  1/1975  Robota ............................ 260/651 F Primary Examiner—C. Davis
Attorney, Agent, or Firm—William A. Simons; Thomas P. O'Day; F. A. Iskander

[57] ABSTRACT

An improvement in the process for making para-chlorobenzotrifluoride by the fluorination of a mixture of the para- and meta- isomers of chlorobenzotrichloride wherein the fluorination reaction is stopped before the complete conversion of the para- and meta- isomers occurs so that the relative amount of meta- isomer of chlorobenzotrifluoride produced will be reduced.

3 Claims, 1 Drawing Figure

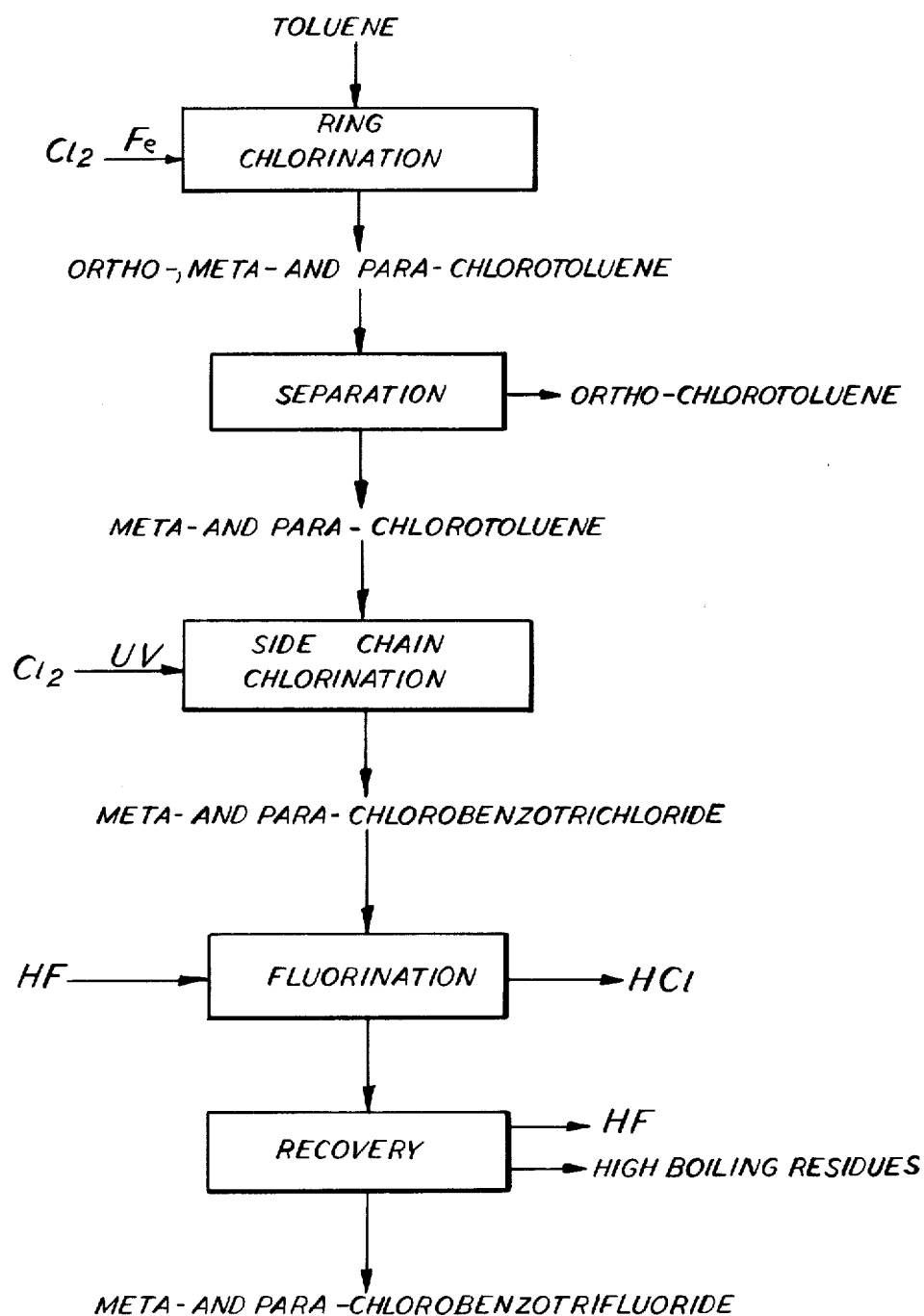

PROCESS FOR PRODUCING HIGH PURITY PARA-CHLOROBENZOTRIFLUORIDE

BACKGROUND OF THE INVENTION

A. Field of Invention

This invention relates to an improvement in the method for preparing para-chlorobenzotrifluoride.

B. Description of the Prior Art

The compound para-chlorobenzotrifluoride (sometimes referred to herein as PCBTF) is used presently for various commercial applications, one of the most valuable being an intermediate in making herbicides, particularly those used on soybeans. As shown in the drawing, PCBTF is conventionally produced by a multi-step process starting with toluene. In this process, toluene is reacted with gaseous chlorine in the presence of iron powder to give ring chlorination which results in a mixture of the ortho-, meta- and para- isomers of chlorotoluene. The orthochlorotoluene is normally the predominantly produced isomer, with the para- isomer produced in a somewhat lesser amount. The meta- isomer is produced in very small amounts, usually from about 10% by weight to about 0.5% by weight of the corresponding para- isomer. In the next step, the ortho- isomer is separated from the meta- and para- isomers, usually by distillation. This separation is easily accomplished because the ortho- isomer has a slightly higher boiling point than the other two isomers, while both the para- and meta- isomers have essentially the same boiling point. Later, the mixture of these latter two isomers are reacted with gaseous chlorine under ultraviolet light to chlorinate the side chain carbon of the chlorotoluene molecule. Then, the resulting mixture of the para- and meta- isomers of chlorobenzotrichloride is fluorinated, usually with excess anhydrous hydrogen fluoride with or without a catalyst, to produce both PCBTF and meta-chlorobenzotrifluoride (sometimes referred to herein as MCBTF). This mixture of PCBTF and MCBTF is recovered together by conventional methods, normally by a phase separation to remove excess unreacted hydrogen fluoride followed by a distillation and condensation of the mixture to separate out any high-boiling residues (e.g., partially fluorinated products).

A problem with the above-described process is that it usually produces MCBTF in sufficient amounts to constitute a substantial impurity to PCBTF. However, in some commercial uses of PCBTF, such as an intermediate in making herbicides, a very low level of impurities such as MCBTF is desirable. And, yet, in each step of the above process, the corresponding meta- and para- isomers have essentially the same physical properties and, therefore, separation of these isomers is very difficult. In fact, all known methods are impractical on large-scale commercial levels.

Therefore, a need exists in the art to develop a way of reducing the amounts of meta- isomer present in PCBTF. Specifically, the present invention accomplishes this by controlling the extent of the above-mentioned fluorination step, thereby producing an improved, commercially acceptable product.

BRIEF SUMMARY OF THE INVENTION

Accordingly, the present invention is an improvement in the process of making para-chlorobenzotrifluoride so that a commercially acceptable product having a very low level of meta-chlorobenzotrifluoride present can be produced. Specifically, the improvement of this process comprises terminating the fluorination reaction of a mixture of the para- and meta- isomers of chlorobenzotrichloride before complete conversion of para- and meta- isomers occurs so that the relative amount of the meta- isomer of chlorobenzotrifluoride produced will be reduced.

BRIEF DESCRIPTION OF THE DRAWING

The drawing shows a flow chart of a multi-step process relating to the production of para-chlorobenzotrifluoride from toluene.

DETAILED DESCRIPTION OF THE INVENTION

As stated above, the present invention is concerned with controlling the extent of the fluorination step. This step has two reactants, the crude para-chlorobenzotrichloride product formed by the preceding step and hydrogen fluoride.

Besides the para-chlorobenzotrichloride, which makes up a major portion of the crude product (usually about 85% to 99% by weight), this product also contains a minor portion of meta-chlorobenzotrichloride (usually about 10% to 0.1% by weight) and, possibly, very small amounts of unidentified high-boiling impurities, presumably, benzo compounds which are only partially chlorinated on the side chain carbon. Also, a trace of the corresponding ortho- isomer may be present.

The hydrogen fluoride is utilized from any commercially known liquid or gaseous source. It is preferred to use liquid anhydrous hydrogen fluoride because of its relative ease of use as compared with the gaseous form. In practice, most hydrogen fluoride reactions are carried out in the liquid phase because reactions involving the gas phase are extremely slow.

During this fluorination step, in order to convert the three chloride atoms on the side chain carbon to fluorides, it is stoichiometrically necessary to have three moles of hydrogen fluoride per mole of chlorobenzotrichloride compound. However, it is preferred to use a stoichiometric excess of hydrogen fluoride. By doing this, the crude chlorobenzotrichloride becomes the limiting reactant and the rate of reaction is dependent only on its concentration. Normally, a molar ratio ranging from about 5:1 to about 30:1 of hydrogen fluoride to chlorobenzotrichloride is preferred, and, most preferably, a molar ratio of about 20:1 is used.

The present invention is based on the discovery that in the fluorination reaction, the rates of reaction of the corresponding para- and meta- isomers are different. The para- isomer reacts much faster than the meta- isomer. From this fact, it was determined that if the reaction was stopped at a certain point of time, the para- isomer could be obtained in good yield, while the amount of meta- isomer would not yet be fully converted and MCBTF would be formed in a reduced yield.

In particular, it has been found that both the para- and meta- isomers react according to the following reaction sequence (shown only for the para- isomer):

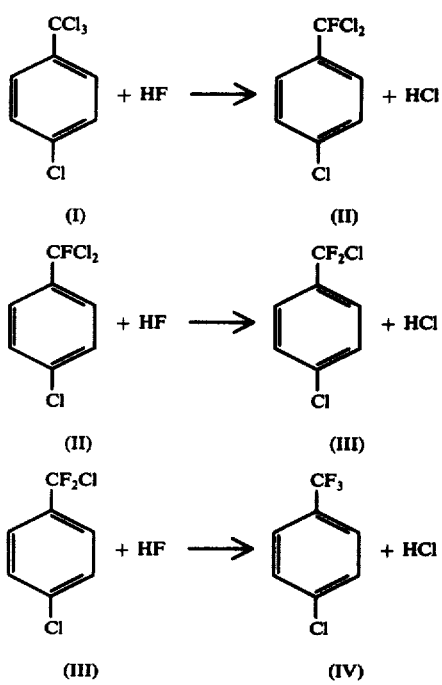

The rate of reaction of (I) with HF to give (II) is very fast. The rate of reaction of (II) with HF to give (III) is somewhat slower, while the rate of reaction of (III) with HF to give (IV) is the slowest reaction and the controlling step. Correspondingly, it has been discovered that, although the meta- isomer reacts in the same sequence, the rates for each step are slower than the para reaction. For example, it has been calculated that when the reaction is carried out under conditions such as at atmospheric pressure, and at an HF:chlorobenzotrichloride molar ratio of 20:1 with a reaction temperature of 12°–15° C, the ratio of the rate of conversion of (III) to (IV) relative to the rate of conversion of the corresponding meta- isomer is about 25:1. In other words, the rate of formation of PCBTF is 25 times faster than the rate of formation of MCBTF under these conditions.

It can be seen that the MCBTF concentration only starts to build up to any appreciable degree during the final stages of PCBTF reaction (i.e., when only a final few percent or less than one percent of (III) remain in the mixture to be converted to (IV)). Therefore, by terminating the reaction before it would stop naturally, the level of MCBTF concentration can be maintained below a desired level with most of the meta- isomer remaining as partially fluorinated compounds like (II) and (III). Depending upon when the reaction is stopped, a small loss in yield of PCBTF will be sustained as some unconverted (III) will remain in the reaction mixture. However, both (III) and the analogous, partially fluorinated meta- isomers have much high-boiling points than PCBTF and MCBTF and can easily be separated, most suitably by distillation.

For the present invention, it is preferred not to allow the para- isomer conversion go over 99%, and more preferably, not over 99.6% by weight. Likewise, it is preferred that the reaction termination point be chosen so that no more than 50% by weight of said meta-chlorobenzotrichloride is converted into MCBTF, and more preferably, where no more than 25% by weight of said meta-chlorobenzotrichloride is converted into MCBTF. This point can easily be determined by either monitoring the amount of para conversion into PCBTF and/or the increasing amount of MCBTF concentration using conventional chemical analytical techniques.

Normally, the reaction is terminated by merely stopping agitation of the reaction mixture and allowing two layers to be formed. The upper, lighter layer contains substantially unreacted hydrogen fluoride and the lower, heavier layer contains the organic products, particularly, para-chlorobenzotrifluoride. The lower organic layer is separated from the HF layer and then the PCBTF is recovered from any contaminants by conventional methods. But, as stated above, MCBTF cannot easily be removed from PCBTF and, therefore, any produced by the fluorinated reaction will remain with the PCBTF.

The preferred mode of PCBTF recovery involving this lower layer involves, first, neutralizing the layer to remove any small quantities of residual HF which may have been retained. Preferably, this is accomplished by adding aqueous potassium hydroxide to the layer. Next, the neutralized layer can be subjected to conventional distillation and condensation steps whereby higher boiling, partially fluorinated compounds (both meta- and para- type compounds), can be easily removed as a distillation residue. After such purification steps, the recovered PCBTF having a reduced level of MCBTF is obtained.

It should be noted that, while the above recovery process is a preferred embodiment of the present invention, other conventional recovery methods (e.g., extraction techniques) may be employed.

The reaction parameters of the fluorination step other than the point at where the reaction is stopped are not critical limitations of the present invention. Any conventionally known method for carrying out this step, such as that outlined in U.S. Pat. No. 3,136,822, can be employed. Included are those methods under super-atmospheric or atmospheric pressure, with or without catalysts and using various temperatures and ratios of the two reactants.

For example, the present invention can be carried out at any conventionally employed temperature. The upper temperature limitation is preferably such that the reactants do not volatilize or the reaction proceeds at such a rate that it is uncontrollable. The lower temperature limitation is preferably such that reaction occurs at an economically fast enough rate. Normally, when the reaction is carried out under atmospheric conditions, the temperature does not exceed 20° C, preferably ranging from about 12°–15° C. Under super-atmospheric pressure, it may be desirable to use higher temperatures.

The reaction can be run with or without a catalyst. No catalyst is required, but for a faster reaction time, any conventional one may be desired. Specifically, the use of a catalyst should shorten the rates of conversion for both PCBTF ane MCBTF, however, the relative difference in those rates will not be substantially affected.

It should be understood that the two reactants should be thoroughly dispersed or mixed together. Usually, this is done by conventional agitation means. In a preferred embodiment, the reaction mixture is continuously agitated during addition of the crude para-chlorobenzotrichloride into the HF and during the total reaction period. Agitation is important in view of the fact that the HF is only slightly soluble with either chlorobenzotrichloride or chlorobenzotrifluoride, and, therefore, without agitation the reaction would occur only at the interface of the two phases.

During the reaction, the hydrogen chloride gas which is formed as a by-product is continuously removed. The hydrogen fluoride which may also be vaporized under the conditions of the reaction is preferably condensed and returned to the reaction mixture. In addition, it is preferred that substantially all of the organic material which is carried up by the evolved hydrogen chloride be returned to the reaction temperature. Normally, these results are accomplished by the use of a hydrogen fluoride condenser which allows the evolved hydrogen chloride to pass through and out of the reaction system.

Finally, it should be understood that while the steps as shown in the drawing can be used to make the para-chlorobenzotrichloride starting material, such steps and their parameters are not critical parts of the present invention. Other processes which make this particular starting material are also encompassed within the scope of this invention.

The following examples are given to illustrate the process of the present invention. All percentages are by weight unless otherwise indicated.

EXAMPLE 1

To 20 moles of anhydrous liquid HF was slowly added 1 mole of mixed chlorobenzotrichloride having the composition 91.5 wt.% para-chlorobenzotrichloride, 7.9 wt.% meta-chlorobenzotrichloride and 0.5 wt.% ortho-chlorobenzotrichloride, while gently agitating the reaction mixture. Gaseous HCl is given off during the reaction and HF carried with the HCl is refluxed back to the reactor through an overhead condenser. The reaction mixture was maintained at 5° C. The reaction mixture was agitated for an additional 2 hours and then the reaction temperature raised to 15° C. The reaction was stopped after 11 hours and organic layer was phased and neutralized. The organic phase was distilled in a 10 plate Oldershaw column. The table below gives the product analysis before and after distillation.

| Compound | Crude Product Before Distillation | Distilled Product After Distillation |
| --- | --- | --- |
| PCBTF | 92.5 | 99.4 |
| MCBTF | 0.5 | 0.5 |
| Ortho-chlorobenzotrifluoride | Trace | |
| Compound (III) - | | |
| Para | 1.0 | |
| Meta | 5.8 | |
| Ortho | 0.2 | |
| Low Boilers | | 0.1 |

This example illustrates that by stopping the reaction at about 99% conversion of para-chlorobenzotrichloride to para-chlorobenzotrifluoride only about 8.4% of the meta-chlorobenzotrichloride was converted to MCBTF. Obviously, extending the reaction further to get 100% conversion of para-chlorobenzotrichloride to PCBTF will substantially increase the formation of MCBTF.

EXAMPLE 2

The experiment of Example 1 was repeated using feed para-chlorobenzotrichloride having approximately 1.1% meta-chlorobenzotrichloride. The reaction was carried out for 18 hours giving a conversion of the para-isomer about 99.6%. The product after distillation contained 0.1% MCBTF, thus, showing over a tenfold reduction in the meta impurity.

What is claimed is:

1. In a process for making para-chlorobenzotrifluoride wherein a mixture comprising meta- and para-chlorobenzotrichloride is reacted with hydrogen fluoride, the improvement which comprises
    terminating the fluorination reaction when no more than 99% by weight of said para-chlorobenzotrichloride has been converted to para-chlorobenzotrifluoride and no more than 50% by weight of said meta-chlorobenzotrichloride has been converted into meta-chlorobenzotrifluoride.

2. The process of claim 1 wherein said para-chlorobenzotrifluoride is recovered by
    separating excess hydrogen fluoride from an organic phase containing said para-chlorobenzotrifluoride,
    neutralizing hydrogen fluoride entrapped within said organic phase,
    distilling said organic phase to separate out said para-chlorobenzotrifluoride and meta-chlorobenzotrifluoride from high-boiling organic residues.

3. The process of claim 1 wherein said fluorination reaction is terminated when no more than 99.6% by weight of said para-chlorobenzotrichloride has been converted to para-chlorobenzotrifluoride and no more than 25% by weight of said meta-chlorobenzotrichloride has been converted into meta-chlorobenzotrifluoride.

* * * * *